United States Patent [19]

Volke et al.

[11] Patent Number: 5,466,724
[45] Date of Patent: Nov. 14, 1995

[54] ADHESIVE COMPOSITION FOR A WOUND DRESSING

[75] Inventors: Robert W. Volke; Debashish Chakravarthy, both of Garrettsville, Ohio

[73] Assignee: Variseal Corporation, Parkman, Ohio

[21] Appl. No.: 406,742

[22] Filed: Mar. 20, 1995

Related U.S. Application Data

[60] Continuation-in-part of Ser. No. 276,443, Jul. 18, 1994, which is a division of Ser. No. 69,784, Jun. 1, 1993, abandoned.

[51] Int. Cl.⁶ .................. C08L 9/26; C08L 3/02; C08L 5/04; A61F 13/02
[52] U.S. Cl. .................. 523/111; 424/443; 428/355; 428/521; 524/35; 524/45; 524/55; 524/375; 524/534; 525/54.31; 602/54; 602/52
[58] Field of Search .................. 424/443; 428/343, 428/355, 521; 523/105, 111, 115; 524/22, 28, 35, 45, 52, 54, 55, 575, 534; 525/54.31; 602/52, 54, 344

[56] References Cited

U.S. PATENT DOCUMENTS

| | | | |
|---|---|---|---|
| 3,339,546 | 9/1967 | Chen | 128/156 |
| 3,973,563 | 8/1976 | Green et al. | 128/156 |
| 4,166,051 | 8/1979 | Cilento et al. | 260/17.4 CL |
| 4,192,785 | 3/1980 | Chen et al. | 260/17.4 GC |
| 4,318,742 | 3/1982 | Lokken | 106/35 |
| 4,393,080 | 7/1983 | Pawelchak et al. | 428/355 |
| 4,477,325 | 10/1984 | Osburn | 204/159.12 |
| 4,505,976 | 3/1985 | Doehnert | 428/355 |
| 4,551,490 | 11/1985 | Doyle | 524/22 |
| 4,743,499 | 3/1988 | Volke | 428/317.3 |
| 4,855,335 | 8/1989 | Neperud | 523/111 |
| 4,952,618 | 8/1990 | Olsen | 524/17 |
| 5,006,401 | 4/1991 | Frank | 428/231 |

*Primary Examiner*—Peter A. Szekely
*Attorney, Agent, or Firm*—Reese Taylor

[57] ABSTRACT

An adhesive composition suitable for wound dressing and other medical applications comprising a mixture of polyisobutylene and a rubber polymer selected from the group consisting of random styrene butadiene rubber (SBR) and halobutyl rubber so as to form a rubbery elastomer base matrix, and at least one hydrocolloid. The addition of the SBR or halobutyl rubber to the elastomer base offsets the possible degradation of the polyisobutylene upon sterilization, and therefore, helps to maintain the integrity of the composition. Water soluble hydrocolloid gums and water swellable cohesive strengthening agents are dispersed within the base matrix and may carry a pharmaceutical agent to be dispensed directly to a wound site.

9 Claims, No Drawings

ADHESIVE COMPOSITION FOR A WOUND DRESSING

RELATED PATENT APPLICATIONS

This application is a continuation in part application of Applicant's earlier filed application Ser. No. 276,443 filed Jul. 18, 1994, pending which is a division of Applicant's earlier filed application Ser. No. 069,784 filed Jun. 1, 1993, now abandoned.

TECHNICAL FIELD

The present invention relates to an adhesive composition suitable for use in wound dressings and other medical applications. More particularly, the present invention relates to a hydrocolloid adhesive composition suitable for a wound dressing which will not disintegrate upon use and thereby leave at least part of the adhesive composition in the wound bed. Specifically, the present invention relates to a hydrocolloid adhesive composition comprising a mixture of a low molecular weight polyisobutylene and a random copolymer of styrene and butadiene having a high styrene content (hereinafter referred to as "styrene-butadiene rubber" or "SBR") or a halogenated butyl rubber (hereinafter referred to as "halobutyl rubber"), the mixture having at least one hydrocolloid powder dispersed therein. The adhesive may also be utilized to dispense medication to the wound site.

BACKGROUND OF THE INVENTION

Wound dressings have long been used in the art to protect and help heal wounds or skin eruption on areas of the body that have been injured. Generally, it is well known to combine an adhesive material with a plastic layer or film or with a foam layer or both. For instance, Volke U.S. Pat. No. 4,743,499, owned by the assignee of record, is directed toward a hydrocolloid laminate which comprises a lower layer of hydrocolloid adhesive and an upper layer of flexible open-cell polymer foam. A first film layer is interposed between the adhesive layer and the foam layer while a second film layer is provided on the foam layer on the side opposite the first film layer.

With respect to adhesive compositions used for wound dressings, various compositions have long been known in the art. For example, Chen U.S. Pat. No. 3,339,549 discloses a blend of rubbery elastomer such as polyisobutylene and one or more water soluble or water swellable hydrocolloids such as a powdery mixture of pectin, gelatin, and carboxymethyl-cellulose. The adhesive mass has a water insoluble material applied to one surface. Such a dressing is commercially available from E.R. Squibb & Sons, Inc. under the trademark Stomadhesive and is used as a skin barrier around stomas to prevent skin breakdown by the corrosive fluids discharged by the stoma.

Similarly, Cilento U.S. Pat. No. 4,166,051 discloses an ostomy composition for use around the stoma consisting of a homogeneous mixture of a pressure sensitive adhesive component such as natural rubber or polyisobutylenes, as well as mineral oil, and one or both of a hydrocolloid gum or cohesive strengthening agent. The mineral oil is noted as permitting the composition to be easily shaped according to the particular need.

Pawelchak et al. U.S. Pat. No. 4,393,080 discloses a medical grade adhesive composition comprising a homogenous blend of one or more pressure sensitive adhesive materials and one or more natural or synthetic polymers which are capable of developing elastomeric properties when hydrated such as gluten and long chain polymers of methyl vinyl ether/maleic acid. The composition also preferably includes one or more water soluble hydrocolloid gums and/or one or more water swellable cohesive strengthening agents.

In hydrocolloid adhesive compositions of these types, the polyisobutylene is hydrophobic but provides the adhesive properties required of the dressing. The hydrocolloid powders are hydrophilic, and therefore, when the adhesive composition is placed in contact with an exuding wound, the water from the wound, upon penetrating the adhesive, is absorbed by the hydrocolloid particles.

However, a major problem with these compositions is their susceptibility to breakdown and fragmentation upon exposure to the wound exudate and body fluids. Notably, the hydration of the hydrophilic hydrocolloid particles begins at the adhesive/wound interface and progressively hydrates deeper into the adhesive composition. The hydrocolloid particles typically hydrate to 20 or 30 times their weight in water, producing large domains of water or fluid suspended in the polymer phase. Thus, with time, due to the large difference in the surface tension between the polymer phase and the liquid phase, there is a phase reversal at that part of the adhesive near the adhesive/wound interface wherein the water or fluid phase becomes dominant and has small fragments or pieces of pure polymer therein.

At this point, the adhesive composition has disintegrated such that it no longer is a solid polymer adhesive, but rather, becomes a paste or gel on the surface of the wound. Hence, when the dressing is removed, a residue remains in the wound requiring removal, typically by irrigation or washing. Furthermore, when this phase reversal occurs, the dressings have been known to lift off the wound and allow leakage of exudate.

Several attempts have been made heretofore to improve the integrity of the hydrocolloid adhesive composition. For example, a mixture of low and high molecular weight polyisobutylenes, mixed so that both polymers are in a continuous phase, has been used as a wound dressing and is available from the assignee of record under the tradename Duoderm. Similar to the composition described in Chen U.S. Pat. No. 3,339,549, this composition includes a blend of gelatin, pectin (citrus), and sodium carboxymethyl cellulose embedded in the matrix of the dressing at approximately 40 percent by weight. The ingredients are not in a continuous phase, but are powders in their particulate form.

Chen et al. U.S. Pat. No. 4,192,785 describes incorporating into the adhesive composition a cohesive strengthening agent such as natural or synthetic fibrous material, finely divided cellulose, cross-linked dextran, and cross-linked carboxymethylcellulose or a starch-acrylonitrile graft copolymer. The cohesive strengthening agent is reported to control the rate of hydration of the composition thereby increasing resistance to disintegration by body fluids.

Doyle et al. U.S. Pat. No. 4,551,490 also discusses the use of cohesive strengthening agents to control the rate of hydration of the composition. Moreover, the patent indicates that styrene radial or block type copolymers such as styrene-butadiene-styrene (S-B-S) and styrene-isoprene-styrene (S-I-S) block type copolymers may be used as a component of the pressure sensitive composition. These block type copolymers are available from Shell Chemical Co. under the tradename Kraton. No reason is given for their use.

A composition similar to the adhesive composition disclosed in Doyle et al. U.S. Pat. No. 4,551,490 is available from the assignee of that patent, E.R. Squibb and Sons, Inc., under the tradename Control Gel Formula (CGF). This composition is a mixture of polyisobutylene, a thermoplastic polymer such as styrene-butadiene-styrene (S-B-S) block copolymer, and hydrophilic powders. The S-B-S block copolymer is reported to create a thermodynamically stiff, three-dimensional matrix with embedded polyisobutylene and hydrophilic powders. This three-dimensional matrix is said to be resistant to phase reversal as described hereinabove because of its three-dimensional structure and the polarity of the S-B-S block copolymer moiety.

Neperud U.S. Pat. No. 4,855,335 also discloses an adhesive composition consisting essentially of a homogeneous mixture of one or more polyisobutylenes and a styrene copolymer such as styrene-butadiene-styrene (S-B-S) or styrene-isoprene-styrene (S-I-S) block copolymers as well as a tackifying resin, mineral oil, and a water insoluble, but water swellable hydrocolloid. However, it further includes ethylene vinyl acetate copolymer which is noted to increase the dimensional stability of the final composition.

Olsen U.S. Pat. No. 4,952,618 is directed toward a hydrocolloid adhesive composition comprising a rubbery elastomer having water soluble or water swellable hydrocolloid particles dispersed therein, at least a portion of which are polycationic hydrocolloid particles. The patent teaches that the compositions have an absorbency value of at least 180 percent and an integrity value of at least 60 percent.

Thus, none of the known art has heretofore provided an adhesive composition which maintains the integrity of the composition through the use of polyisobutylene and the addition of styrene-butadiene random copolymer (SBR) or halobutyl rubber.

SUMMARY OF THE INVENTION

It is therefore, an object of the present invention to provide an adhesive composition adaptable for use in wound dressings and other medical applications such as ostomy care and incontinence.

It is another object of the present invention to provide an adhesive composition, as above, having increased resistance to breakdown or disintegration upon exposure to wound exudate and/or water.

It is yet another object of the present invention to provide an adhesive composition, as above, employing a rubbery elastomer base which strengthens the matrix of the composition to improve the integrity of the adhesive composition.

At least one or more of the foregoing objects of the present invention, together with the advantages thereof over the prior art relating to wound dressings, which shall become apparent from the specification which follows, are accomplished by the invention as hereinafter described and claimed.

In general, the present invention provides an adhesive composition comprising a rubbery elastomer base comprising a mixture of polyisobutylene and a polymer selected from the group consisting of styrene-butadiene random copolymer (SBR) and halobutyl rubber, and at least one hydrocolloid dispersed therein.

The present invention also provides a wound dressing comprising a plastic film/foam layer and an adhesive bonded to one side thereof, the adhesive comprising a mixture of polyisobutylene and a polymer selected from the group consisting of styrene-butadiene random copolymer (SBR) and halobutyl rubber, said adhesive mixture having at least one hydrocolloid dispersed therein.

The present invention further provides a wound dressing comprising a plastic film/foam layer and an adhesive bonded to one side thereof, the adhesive comprising a mixture of polyisobutylene and a polymer selected from the group consisting of solution polymerized random copolymers of styrene and butadiene.

PREFERRED EMBODIMENT FOR CARRYING OUT THE INVENTION

The adhesive composition of the present invention is suitable for a variety of medical applications and, in particular, is suited for use in wound dressings. As is well known, a wound dressing generally comprises a plastic layer or film or a foam layer having a medically effective adhesive material bonded to one side thereof. Such dressings may be useful in treating wounds, skin lesions, burns and stomas regardless of the cause.

The adhesive composition of the present invention generally comprises a homogeneous mixture of one or more polyisobutylenes and either styrene-butadiene random copolymer (SBR) or halobutyl rubber, at least one water soluble or water swellable hydrocolloid gum or cohesive strengthening agent, and optionally, fillers such as pigments, tackifiers, or pharmaceutical agents. Such a composition has been found to have an increased resistance to disintegration and fragmentation upon exposure to significant amounts of wound exudate.

The mixture of polyisobutylene and styrene-butadiene rubber (SBR) or halobutyl rubber form the rubbery elastomer base of the composition. This mixture functions to provide the adhesive properties for the composition. That is, it provides dry tack and holds the entire composition together. Notably, it is believed that the mixture forms a crosslinked matrix which is three dimensional in character as detailed hereinbelow.

Preferably, the polyisobutylene rubber employed in the composition has a low viscosity average molecular weight, on the order of from about 36,000 to 58,000 (Flory). Such polyisobutylenes are commercially available under the trademark VISTANEX from Exxon as grades LM-MS and LM-MH.

The SBR which may be employed in the composition is preferably a random copolymer of styrene and butadiene containing relatively high amounts of styrene as compared to other random copolymers of styrene and butadiene. From about 23 to about 50 percent by weight of styrene in the SBR is preferred. The random copolymers of styrene and butadiene may be either emulsion polymerized or solution polymerized, although solution polymerized random SBR is preferred for reasons explained hereinbelow.

One emulsion polymerized random SBR, having about 48 percent by weight of styrene, is commercially available from The Goodyear Tire and Rubber Company under the tradename Plioflex 1028. This SBR is a food grade SBR manufactured in an emulsion type polymerization process and is, therefore, typically referred to as an emulsion SBR. The polymerization process employed to make this SBR involves the use of organic fatty acid-based or rosin acid-based emulsifiers and coagulants. Consequently, the final product has about 4 to 5 percent of this acid distributed in the polymer matrix.

Because non-rubber excipients such as fatty acid emulsifiers and coagulants remain in the polymer matrix, emulsion random styrene-butadiene rubbers such as Plioflex 1028 typically possess a faint acrid odor. Depending upon the application, use of components having an acrid odor may be unsatisfactory or even unacceptable in some instances.

Furthermore, it has been found that the acrid odor intensifies upon sterilization of the wound dressing by gamma radiation, the preferred means for sterilizing wound dressings in medical applications as is detailed hereinbelow. In fact, the odor may reach unacceptable levels in some cases. Moreover, since wound dressing are typically packaged in air tight containers, it is possible that the odor might build up with the age of the product and subject the ultimate user of the product to an intense acrid odor as soon as the package containing the wound dressing is opened.

While the odor should not be seen as necessarily eliminating the use of emulsion random styrene-butadiene rubbers in every instance, it is believed that all random copolymers of styrene and butadiene made by the emulsion process possess the odor. Emulsion processes by their very nature require the use of fatty acid or rosin acid based emulsifiers and the use of coagulants.

Solution polymerized random styrene-butadiene rubbers do not have this acrid odor. Two solution polymerized random styrene-butadiene rubbers, having about 48 and 35 percent by weight of styrene, are commercially available from Housmex under the tradename Solprene 303 and from Firestone under the tradename Duodrene 709, respectively. These SBRs are thermoset materials and are produced by a solution polymerization process. In that process, the polymerization reaction is conducted in a homogeneous solution in a hydrocarbon solvent. The process uses no excipients such as emulsifiers, stabilizers or coagulants.

The halobutyl rubber which may be employed in the composition is preferably bromobutyl rubber having a bromine content of from about 0.9 to about 3 percent by weight in the bromobutyl rubber. Similar to styrene-butadiene rubber, halobutyl rubber is a highly polar rubber which may be effectively blended with the non-polar polyisobutylene rubber. One such bromobutyl rubber, having a bromine content of about 2.1 percent is commercially available from Polysar under the tradename BB2030.

One or more hydrocolloids are dispersed within the composition. The hydrocolloids may include compounds such as water soluble hydrocolloid gums and/or water swellable cohesive strengthening agents. These compounds perform the dual function of controlling the rate of hydration of the adhesive composition by absorbing fluids and strengthening the composition by preventing erosion of the adhesive composition by biological fluids. The hydrocolloids may also function as drug delivery agents to dispense medication to the wound area. Suitable hydrocolloid gums may include, but are not necessarily limited to, pectin, gelatin, sodium carboxymethylcellulose, salts of alginic acid, guar gum, locust bean gum, gum karaya, and mixtures thereof. A mixture of these non-soluble gums are preferably used as the hydrocolloid. Suitable cohesive strengthening agents include finely divided cellulose, alginate fibers, crosslinked dextran, cross-linked carboxymethylcellulose, starch-acrylonitrile graft copolymer or mixtures thereof. Biodegradable cross-linked dextran is preferred as a cohesive strengthening agent for the adhesive composition and is prepared by crosslinking dextran with cyanogen bromide. Fillers such as tackifiers, pigments, and other ingredients may be added in suitable amounts as needed. Where the hydrocolloid is used as a drug delivery agent, a pharmaceutically effective amount of a pharmaceutical agent can also be added. The hydrocolloid carries the pharmaceutical agent within the adhesive as required.

The adhesive compositions of the present invention desirably include from about 60 to about 90 parts by weight polyisobutylene and from about 10 to about 40 parts by weight of a polymer selected from the group consisting SBR and halobutyl rubber to comprise 100 parts by weight of the rubber elastomer base. The hydrocolloids comprise from about 12 percent to about 50 percent by weight of the adhesive.

With reference to Table I, eleven such adhesive compounds have been shown. The first six compounds (Compounds A–F) employed emulsion polymerized random SBR as an ingredient to form the elastomeric rubber base. The last five compounds (Compounds G–K) employed bromobutyl rubber as an ingredient to form the elastomeric rubber base. The last two compounds (Compounds L-M) employed solution polymerized random SBR as an ingredient to form the elastomeric rubber base. The adhesive compositions in Table I are based upon parts by weight, rather than parts per hundred rubber, and accordingly, the numerical values provided are different than the ranges provided hereinabove. However, it will be appreciated that the values do fall within the percentage ranges provided hereinabove upon proper calculation.

TABLE I

| | Adhesive Composition (parts by weight) | | | | | | | | | | | | |
|---|---|---|---|---|---|---|---|---|---|---|---|---|---|
| | A | B | C | D | E | F | G | H | I | J | K | L | M |
| SBR[a] | 20 | 20 | 20 | 20 | 20 | 20 | — | — | — | — | — | 30 | 30 |
| BBR | — | — | — | — | — | — | 20 | 20 | 20 | 20 | 20 | — | — |
| Polyisobutylene[b] | 55 | 55 | 55 | 55 | 55 | 55 | 55 | 55 | 55 | 55 | 55 | 34 | 38 |
| Butyl Hydroxy Toluene | 0.7 | 0.7 | 0.7 | 0.7 | 0.7 | 0.7 | 0.7 | 0.7 | 0.7 | 0.7 | 0.7 | 0.5 | 0.5 |
| Pectin | 12 | 14 | — | — | — | — | — | — | — | — | 12 | 12 | 6 |
| Gelatin | 12 | 7 | — | — | — | — | — | — | — | — | 7 | 7 | 10 |
| Carboxymethyl Cellulose | 4 | 20 | — | — | — | — | — | — | — | — | 7 | 7 | 5 |
| Starch-Acrylonitrile Graft Copolymer[c] | — | — | 17 | — | — | — | — | — | — | 17 | — | — | — |
| Dextran Beads | — | — | — | 17 | — | — | — | — | 17 | — | — | — | — |
| Aliginate Salts | — | — | — | — | 10 | — | — | 10 | — | — | — | 9 | 10 |
| Aliginate Fibers | — | — | — | — | 1.5 | — | — | 1.5 | — | — | — | — | — |
| Carrageenan[d] | — | — | — | — | 10 | 10 | 10 | 10 | — | — | — | — | — |
| Glucomannin[e] | — | — | — | — | — | 10 | 10 | — | — | — | — | — | — |

[a]Compounds A–F are emulsion SBRs (Plioflex 1028); Compounds L–M are solution SBRs (L = Durodene 709; M = Solprene 303)
[b]Vistanex LMMH
[c]D-242 from Grain Processing, Inc. Muskateen, Iowa
[d]K Carrageenan HGP
[e]Konjac (dietary root)

To manufacture the adhesive composition, the polyisobutylene and SBR are mixed on a two roll mill to effect a completely homogeneous mixture of the two polymers where the two polymer phases are continuous but separate. When halobutyl rubber is substituted for SBR, the same manufacturing process may be employed, the two polymer phases being continuous but separate. The hydrocolloid gum and/or cohesive strengthening agents are then added in a blade type mixer such as is commercially available from Baker Perkins.

For use in any medical application, the adhesive composition should be sterilized. Preferably, the sterilization process is performed by means of gamma radiation. However, this sterilization process has a pronounced effect on the polyisobutylene rubber. The polyisobutylene polymers are degraded by chain scission to yield a lower average molecular weight composition. This degraded adhesive has an even poorer ability to resist phase reversal and cold flow.

According to the present invention, the addition of the SBR with a high stryene content or halobutyl rubber to the polyisobutylene tends to offset the degradation of the polyisobutylene during sterilization. The SBR or halobutyl rubber is crosslinked by a free radical carbon-carbon bridge, inducing sufficient crosslink density to offset the chain scission induced into the polyisobutylene phase. SBR or halobutyl rubber also provides a lightly crosslinked matrix, three-dimensional in character, which exhibits increased resistance to phase reversal and disintegration and cohesiveness as indicated by a reduction in the cold flow of the composition. It is believed that this is due to the fact that the SBR and halobutyl rubber are film formers and have a more hydrophilic backbone than do the polyisobutylenes. The difference in surface tensions between the elastomer base mixture of polyisobutylene and SBR or halobutyl rubber and the hydrophilic hydrocolloid particles is much less than when other elastomer bases are employed.

As noted hereinabove, the adhesive composition of the present invention may include a pharmaceutically effective amount of a pharmaceutical agent which can be dispensed directly to the wound site. The pharmaceutical agent is carried by the hydrocolloid dispersed within the composition. More particularly, a suitable hydrocolloid or cohesive strengthening agent such a dextran microspheres crosslinked with cyanogen bromide can be employed as the delivery agent.

In order to demonstrate practice of the invention, pigs of like age, gender and weight were provided with six to eight wounds. These wounds were then treated using five distinct dressings, two of which employed the adhesive compositions of the present invention. The other three dressings used three other well known adhesive compositions. Each wound was approximately 2.5 centimeters in diameter and was generally circular. Each pig was treated with at least two of the dressings. Histological evaluations were performed when the wounds were initiated and at 3, 6, 10, 14 and 18 days when the wound dressings were being changed.

More particularly, adhesive compositions A and D from Table I were used in two of the dressings, hereinafter noted as Dressings 1 and 2, respectively, employed to treat the pigs. As noted in Table I, both dressings employ an adhesive composition comprising a mixture of polyisobutylene and a random copolymer SBR and one or more hydrocolloids.

The other three dressings, hereinafter described as Dressings 3, 4 and 5, respectively, were also used to treat the pigs. While the exact composition of each of these dressings are unknown inasmuch as they are considered proprietary by their manufacturers, it is known that none of these dressings include the adhesive composition of the present invention. That is, none of the three other dressings include a mixture of polyisobutylene and random copolymer SBR. It is also believed that none of the three other dressings include a halobutyl rubber. Accordingly, the adhesive compositions of the present invention can be clearly distinguished from the other three dressings.

Furthermore, while the exact compositions of Dressings 3, 4 and 5 are unknown, it is known that Dressings 3 and 4 include a thermoplastic polymer such as styrene-butadiene-styrene (S-B-S) block copolymer commercially available under the tradename Kraton. Moreover, while hydrocolloids such as pectin, gelatin and carboxymethyl cellulose are believed to be used in the adhesive compositions of both Dressings 3, 4 and 5, none of the adhesive compositions are believed to include biodegradable cross-linked dextran beads as discussed hereinabove and which are employed in Dressing 2.

With respect to the tests, histological evaluations were performed on each of the wounds to identify (i) the presence of eschar, (ii) the completion of re-epithelization, (iii) the thickness of the epithelium, (iv) incision width, (v) collagen organization, (vi) the presence of neovascularity, (vii) the absence of acute inflammation, (viii) the absence of chronic inflammation, (ix) the absence of foreign material, and (x) the absence of giant cells.

With respect to Dressing 1, sixteen (16) sections representing eight wounds from three pigs were histologically reviewed. The majority of the sections showed complete re-epithelization with a thin to moderately thick non-keratinized, stratified squamous epithelium which appeared histologically immature. Where present, chronic inflammatory cells were identified superficially around mildly dilated vessels. Acute inflammation was scant. Neovascularity was minimal and superficial. Small areas of foreign material and foreign body reaction were present. Collagen was well organized and minimally cellular. Four sections had small to moderately sized foreign body reaction centers present in the deep dermis with presence of scant amounts of foreign material. Four other sections had a more mature and thicker stratified squamous epithelium.

Eighteen (18) sections representing eight wounds from three pigs were reviewed after having been treated with Dressing 2. The majority of the sections demonstrated complete re-epithelization with a mature appearing keratinized squamous epithelium. Collagenization was very organized, interrupted only by small collections of foreign body type giant cells. Where inflammation was present, it was scant and mononuclear. Neovascularization was, as well, scant and superficial. Two sections showed re-epithelization without eschar formation. The denuded areas showed moderate number of polymorphonuclear cells within the superficial epidermis penetrating approximately one-quarter of the depth of the section. Two other sections were well re-epithelized but had pronounced foreign body type reactions in the deep dermis. Collagenization was preserved.

Seventeen (17) sections representing eight wounds from three separate pigs receiving Dressing 3 treatment were reviewed. The majority of the sections showed complete re-epithelization with squamous epithelium thinner and less mature than that described in the Dressing 2-treated group. Neovascularity was scant but present in the superficial and mid-dermis. Chronic inflammation was patchy. Collagenization was organized but more cellular than the Dressing 2-treated group. Foreign body giant cell aggregates were focal in some sections. Despite the lack of re-epithelization, acute inflammation was not appreciable. Four sections had more pronounced foreign body reaction than the remaining sections. In these sections, medium to large sized aggregates of foreign body type giant cells were identified from the superficial to the deep dermis. Collagenization, in these sections, was less organized.

For Dressing 4, seventeen (17) sections representing eight wounds from three pigs were histologically reviewed. The majority of the sections showed complete re-epithelization with a thin non-keratinized, stratified squamous epithelium. Neovascularity was mild and present superficially and in the deep dermis. Vessels were focally dilated. Chronic inflammation was moderate and located in the upper one-half of the tissues. Acute inflammation was localized within and around reactive foreign body centers located in the deep dermis. These were present in some but not all of the sections and were small to moderate in size. Foreign material was easily identified. Collagenization was patchy but appeared to be more organized than cellular. Two sections had large confluent necrotizing foreign body granulomas present just below the superficial dermis and extending into the deep dermis. Four sections showed incomplete re-epithelization.

Finally, twelve (12) sections representing six wounds from two pigs receiving treatment using Dressing 5 were reviewed. The majority of these sections showed minimal to no greater than 50 percent re-epithelization without eschar formation. On the whole, neovascularity was increased and diffusely present from the superficial to deep dermis. These sections demonstrated striking necrotizing granulomatous foreign body reactions present in the superficial to deep dermis. These were so great in number to be focally confluent. Most sections contained identifiable foreign body material. Collagenization was weak. Three sections were similar in all respects except for the presence of an eschar.

Based upon the results of these evaluations, the dressings were rated as compared to each other in each of the ten identifiable categories. The ratings for these dressings are found in Table II below.

TABLE II

RATINGS FOR DRESSINGS
(1 = BEST/5 = WORST)

| Evaluation | Dressing | | | | |
|---|---|---|---|---|---|
| | 1 | 2 | 3 | 4 | 5 |
| Eschar | 1 | 3(tie) | 3(tie) | 2 | 5 |
| Re-Epithelization | 1 | 2 | 3 | 4 | 5 |
| Thickness of Epithelium | 2 | 1 | 4 | 3 | 5 |
| Incision Width | 4 | 2 | 3 | 1 | 5 |
| Collagen Organization | 1 | 2 | 4 | 3 | 5 |
| Neovascularity | 4(tie) | 3 | 2 | 4(tie) | 1 |
| Acute Inflammation | 1 | 2(tie) | 2(tie) | 4 | 5 |
| Chronic Inflammation | 2 | 1 | 3 | 4 | 5 |
| Foreign Material | 3 | 2 | 1 | 4 | 5 |
| Giant Cells | 2 | 1 | 3 | 4 | 5 |
| TOTALS | 21 | 19 | 28 | 33 | 46 |

Based upon the results of these evaluations, it should be clear that both Dressings 1 and 2 performed better overall than did the other three dressings. One of the two dressings of the present invention was rated the best as compared to the other dressings in all but three of the categories evaluated.

For Compounds L and M, skin irritation screens were conducted in accordance with the guidelines of the Federal Hazardous Substances Act (FHSA) Regulations, 16 C.F.R. §1500 et seq., but were modified to three rather than six animals (rabbits). In the test, 1×1 inch sections from each of these compounds as wound dressings were topically applied to the intact and abraded skin of three rabbits and left in place for a 24-hour period. The test sites were then graded for erythema and edema at 24 and 72 hours after the single application. Typically, commercial wound dressing compounds cause only slight irritation. To evaluate and compare skin irritations, a primary irritation index (P.I.I.) is utilized which is generally based on the sum of various scored reactions and divided by a factor representing the number of scoring intervals multiplied by the number of test parameters. An index number less than 5.00 is sufficient to not be considered a skin irritant, but commercial wound dressing typically are scored below 2.00. For example, the well known dressing Duoderm CGF (Convatec) scored 1.33. Compounds L and M received an P.I.I. score of 1.33 and 1.00, respectively, which indicates that wound dressings prepared from these compounds are at least as safe as commercially available wound dressings with respect to skin irritation. Additionally, toxicity tests preformed on Compounds L and M showed the absence of any systemic toxicity.

In addition to the histological, skin irritation, and toxicity evaluations detailed hereinabove, tests were performed to determine the integrity or resistance to disintegration of the adhesive compositions employed in the dressings. In particular, a 9 percent saline absorption test was performed. In order to perform this test, samples pieces of the adhesive compositions A through G and L through M in Table I were prepared to a thickness of approximately 0.04 inches. One surface was laminated with a 1.0 mil Berteck Nucril plastic film then cut into 1"×1" squares. These test pieces were then immersed in approximately 40 milliliters of 0.9 percent sodium chloride (NaCl) solution for approximately 24 hours. At the end of the 24-hour immersion period, the sample pieces were removed from the test solution, blotted dry and weighed. The weight increase was recorded as the 24 hour absorption. Other weight measurements were made at 1, 2 and 5 hour increments by drip-drying the samples.

The samples were returned to the original 40 mls of test fluid and a magnetic stirrer rod was placed on the bottom of the beaker and stirring started at 100 RPM to erode the swollen adhesive composition. At the end of 6 minutes, the samples were extracted from the beaker, blotted dry and weighed again. This final weight was recorded as the eroded weight.

As a result of these tests, it is clear that Dressings 1 and 2 performed much better inasmuch as their resistance to fragmentation and disintegration were substantially higher than that of the other three dressings. The results of the tests are found in Table III below.

TABLE III

| | 0.9% SALINE ABSORPTION (1" × 1" × .040") | | | | | | | | |
|---|---|---|---|---|---|---|---|---|---|
| | A | B | C | D | E | F | G | L | M |
| Original Weight | 1.00 | 1.00 | 1.00 | 1.00 | 1.00 | 1.00 | 1.00 | 1.00 | 1.00 |
| 1 Hour | 1.32 | 1.73 | 1.56 | 1.11 | 1.25 | 1.47 | 1.09 | 1.26 | 1.35 |
| 2 Hours | 1.40 | 2.16 | 1.91 | 1.20 | 1.40 | 1.56 | 1.20 | 1.49 | 1.55 |
| 5 Hours[a] | 1.71 | 3.22 | 3.12 | 1.41 | 2.12 | 2.11 | 1.59 | 2.36 | 2.41 |
| 24 Hours[b] | 2.68 | 6.68 | 4.64 | 2.76 | 3.93 | 4.20 | 3.71 | 3.37 | 3.57 |
| Start | 2.68 | 6.68 | 4.64 | 2.76 | 3.93 | 4.20 | 3.71 | 3.37 | 3.57 |
| 6 minutes | 2.65 | 6.57 | 4.56 | 2.73 | 3.85 | 4.13 | 3.66 | 3.32 | 3.49 |
| % Eroded | 1.1% | 1.5% | 1.7% | 1.0% | 2.0% | 1.7% | 1.2% | 1.5% | 2.2% |

[a]For Compounds L and M, measurements taken at 6 hours.
[b]For Compounds 1 and M, measurements taken at 22 hours.

Thus it should be evident that the mixture of polyisobutylene and random copolymer SBR or halobutyl rubber is highly effective in helping to maintain the integrity of the composition. The invention is particularly suited for wound dressings, but is not necessarily limited thereto. The adhesive composition of the present invention can be used separately in other medical applications and with other medical appliances such as may be used in the fields of incontinence, ostomy care, and burn dressings.

Based upon the foregoing disclosure, it should now be apparent that the adhesive composition described herein will carry out the objects set forth hereinabove. It is, therefore, to be understood that any variations evident fall within the scope of the claimed invention and thus, the selection of specific component elements can be determined without departing from the spirit of the invention herein disclosed and described. Moreover, the scope of the invention shall include all modifications and variations that may fall within the scope of the attached claims.

What is claimed is:

1. A wound dressing comprising:
   a plastic film layer; and
   an adhesive bonded to one side thereof, said adhesive comprising a mixture of polyisobutylene and a rubber polymer selected from the group consisting of solution-polymerized random styrene butadiene copolymers, said adhesive having at least one hydrocolloid dispersed therein.

2. A wound dressing, as set forth in claim 1, wherein said mixture includes from about 60 to about 90 parts by weight polyisobutylene and from about 10 to about 40 parts by weight rubber polymer to total 100 parts of rubber.

3. A wound dressing, as set forth in claim 1, wherein said hydrocolloid is selected from the group consisting of water soluble hydrocolloid gums and water swellable cohesive strengthening agents.

4. A wound dressing, as set forth in claim 3, wherein said water soluble hydrocolloid gum is selected from the group consisting of pectin, gelatin, sodium carboxymethylcellulose, salts of alginate acid, guar gum, locust bean gum, gum karaya, and mixtures thereof and said water swellable cohesive strengthening agent is selected from the group consisting of finely divided cellulose, alginate fibers, cross-linked dextran including biodegradable cross-linked dextran, cross-linked carboxymethylcellulose, starch-acrylonitrile graft copolymers or mixtures thereof.

5. A wound dressing, as set forth in claim 1, wherein said polyisobutylene is a low molecular weight polyisobutylene.

6. A wound dressing, as set forth in claim 1, wherein said solution polymerized random styrene-butadiene rubber has a high styrene content of from about 23 to about 50 percent by weight.

7. A wound dressing, as set forth in claim 1, further comprising a pharmaceutically effective amount of a pharmaceutical agent.

8. A wound dressing, as set forth in claim 7, wherein said pharmaceutical agent is carried by at least one hydrocolloid.

9. A wound dressing, as set forth in claim 1, wherein said random styrene-butadiene copolymer is odorless.

* * * * *